(12) United States Patent
Pombeiro et al.

(10) Patent No.: US 7,238,838 B2
(45) Date of Patent: Jul. 3, 2007

(54) PROCESS FOR DIRECT CONVERSION OF METHANE INTO ACETIC ACID

(75) Inventors: Armando Pombeiro, Lisbon (PT); João Fraústo Da Silva, Lisbon (PT); Yuzo Fujiwara, Fukuoka (JP); José Silva, Lisbon (PT); Patricia Reis, Lisbon (PT); António F. Palavra, Lisbon (PT)

(73) Assignee: Instituto Superior Tecnico, Lisbon (PT)

( * ) Notice: Subject to any disclaimer, the term of this patent is extended or adjusted under 35 U.S.C. 154(b) by 0 days.

(21) Appl. No.: 10/532,387

(22) PCT Filed: Oct. 15, 2003

(86) PCT No.: PCT/PT03/00015

§ 371 (c)(1),
(2), (4) Date: Nov. 4, 2005

(87) PCT Pub. No.: WO2004/037416

PCT Pub. Date: May 6, 2004

(65) Prior Publication Data

US 2006/0155145 A1 Jul. 13, 2006

(30) Foreign Application Priority Data

Oct. 23, 2002 (PT) ...................... 102859

(51) Int. Cl.
*C07C 53/08* (2006.01)
(52) U.S. Cl. .................................... 562/607
(58) Field of Classification Search ...................... None
See application file for complete search history.

(56) References Cited

FOREIGN PATENT DOCUMENTS

EP 0 560 656 A2 9/1993

OTHER PUBLICATIONS

M. Asadulla, Y. Taniguchi, T. Kitamura, Y. Fujiwara, "One-step carboxylation reaction of saturated hydrocarbons with CO by CO(OAc)$_2$ catalyst under mild conditions," *Applied Catalysis A: General* 194-195 (2000) 443-452.

Mohammad Asadullah, Tsugio Kitumura and Yuzo Fujiwara, "CaCl$_2$-Catalyzed Functionalization of Saturated Hydrocarbons with CO to Carboxylic Acids and Esters," *Journal of Catalysis* 195, 180-186 (2000).

Robert E. Berry, Elaine M. Armstrong, Roy L. Beddoes, David Collison, S. Nigar Ertok, Madeleine Helliwell and C. David Garner, "The Structural Characterization of Amavadin," *Angew. Chem. Int. Ed.* 1999, 38, No. 6.

P. Caravan, Lucio Gelmini, Nicholas Glover, F. Geoffrey Hering, Huali Li, John H. McNeill, Steen J. Rettig, Ika A. Setyawati, Ed Shuter, Yan Sun, Alan S. Tracey, Violet G. Yuen and Chris Orvig, "Reaction Chemistry of BMOV, Bis(maltolato)oxovanadium(IV)-A Potent Insulin Mimetic Agent," *J. Am. Chem. Soc.* 1995, 117, 12759-12770.

Chein-Tein Chen, Jen-Huang Kuo, Chun-Hsin Li, N.B. Barhate, Sang-Wen Hon, Tai-Wei Li, Shi-Deh Chao, Chia-Cheng Liu, Ying-Chieh Li, I-Hsin Chang, Jin-Sheng Lin, Chin-Jing Liu and Y-Chen Chou, "Catalytic Nucleophilic Acyl Substitution of Anhydrides by Amphoteric Vanadyl Triflate," *American Chemical Society*, 2001.

Debbie C. Crans, Haojiang Chen, Oren P. Anderson, and Mary M. Miller, "Vanadium(V)-Protein Model Studies: Solid-State and Solution Structure," *J. Am. Chem. Soc.* 1993, 115, 6769-6776.

Debbie C. Crans, Jason J. Smee, Ernestas Gaidamauskas, and Luqin Yang, "The Chemistry and Biochemistry of Vanadium and the Biological Activities Exerted by Vanadium Compounds," *Chem. Rev.* 2004, 104, 849-902.

Brent J. Hamstra, Andrew L. P. Houseman, Gerard J. Colpas, Jeff W. Kampf, Russell Lobrutto, Wayne D. Frasch, and Vincent L. Pecoraro, "Structural and Solution Characterization of Mononuclear Vanadium(IV) Complexes that Help to Elucidate the Active Site Structure of the Reduced Vanadium Haloperoxidases," *Inorg. Chem.* 1997, 36, 4866-4874.

Galina V. Nizova, Georg Süss-Fink, Sandrine Stanislas, and Georgiy B. Shul'Pin, "Carboxylation of methane with CO or CO$_2$ in aqueous solution catalysed by vanadium complexes," *Chem. Commun.*, 1998 1885-1886.

Patricia M. Reis, Jose Armando L. Silva, Joao J.R. Frausto Da Silva and Armando J. L. Pombeiro, "Amavadine as a catalyst for the peroxidative halogenation, hydroxylation and oxygenation of alkanes and benzene," *Chem. Commun.*, 2000, 1845-1846.

Patricia M. Reis, Jose A. L. Silva, Antonio F. Palavra, Joao J. R. Frausto da Silva, Tsugio Kitamura, Yuzo Fujiwara, and Armando J. L. Pombeiro, "Single-Pot Conversion of Methane into Acetic Acid in the Absence of CO and with Vanadium Catalysts Such as Amavadine," *Agnew. Chem. Int. Ed.* 2003, 42, No. 7 821-823.

Yuki Taniguchi, Taizo Hayashida, Hiroyasu Shibasaki, Dongguo Piao, Tsugio Kitamura, Teizo Yamaji, and Yuzo Fujiwara, "Highly Efficient Vanadium-Catalyzed Transformation of CH$_4$ and CO to Acetic Acid," *Org. Lett.*, vol. 1, No. 4, 1999 557-559.

*Primary Examiner*—Paul A. Zucker
(74) *Attorney, Agent, or Firm*—Brinks Hofer Gilson Lione

(57) ABSTRACT

The invention consists on the utilization of complexes of vanadium (in the +4 and +5 oxidation states) with bi- or poly-dentate ligands coordinated by nitrogen and oxygen (N,O) or by oxygen and oxygen (O,O) atoms, namely derivatives of aminoalcohols, (hydroxyimino)dicarboxylic acids, hydroxypyranones, trifluoroacetic acid, triflic acid or inorganic acid, as catalysts for the direct single-pot conversion, under mild conditions, of methane in acetic acid, either in the absence or in the presence of carbon monoxide, and in the presence of a peroxodisulfate salt (K2S2O8), in trifluoroacetic acid (CF3COOH), according to the general reaction (I).

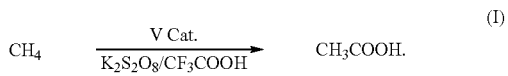

4 Claims, No Drawings

PROCESS FOR DIRECT CONVERSION OF METHANE INTO ACETIC ACID

(A) BACKGROUND, OBJECTIVE AND ADVANTAGES

The conversion of methane in valuable functionalised products constitutes one of the great challenges to modern Chemistry and, in particular, the catalytic synthesis of acetic acid from that gas and carbon monoxide has attracted a current high interest. For this process, a few catalysts based on vanadinum oxides or heteropolyacids have been recently found [1], whereas a lower catalytic activity or selectivity has been recognized for other systems of $Pd(OAc)_2Cu(OAc)_2$ [2], $CaCl_2$ [3], $NaVO_3$ [4], $RhCl_3$ [5,6] (in the presence of $O_2$ [6] with formation also of formic acid and methanol), lanthanide salts [7], $K_2S_2O_8$ [8] or superacids [9].

Moreover, the synthesis of carbonylated products without requiring the use of the noxious carbon monoxide is also of high interest and recently the conversion of methane into methyl trifluoroacetate or methyl acetate has been achieved by using vanadium heteropolyacids [10] or $Cu(OAc)_2$ [11] catalysts. Alternative processes for the conversion of methane into acetic acid by carbonylation of the former by carbon dioxide are also known in heterogeneous catalysis at temperatures in the 100-500° C. range, with Pd [12], Rh [13], Ir [13], Ru [13] or Cu/Co [14,15] catalysts, and they can involve two distinct stages with methanol as an intermediate [16].

The invention under consideration aims to select catalysts and establish a process for the single-pot direct conversion of methane into acetic acid, preferably without the use of carbon monoxide as the carbonylating agent, under mild or moderate temperature and pressure conditions.

Such catalytic systems would present high advantages, in terms of simplicity and energy saving, over the industrial process that is currently followed and involves three distinct complicated and energy expensive stages, i.e. (i) the steam reforming of methane (highly endothermic process, catalysed by a metal catalyst) to form the "synthesis gas", (ii) the catalytic conversion of this gas, also at high temperature, in methanol, and (iii) the carbonylation of this alcohol by carbon monoxide to give acetic acid, usually by the Monsanto process which requires an expensive catalyst (based on rhodium or iridium in a BP-Amoco modified route). The invention in analysis uses a catalyst of vanadium, a much cheaper metal than those above.

(B) INNOVATORY FEATURES

The invention relates to the establishment of new catalytic systems, active under mild or moderate operational conditions, for the direct single-pot conversion of methane into acetic acid, with considerable yields, particularly without the use of carbon monoxide, in contrast with the above methane carbonylating systems.

The inspiration on biological systems for the composition of some of the catalysts is also innovatory, in particular by using models of Amavadine, a natural vanadium complex that exists in some Amanita fungi whose biological function is still unknown. The invention extends, to the carbonylation of methane, the catalytic activity of Amavadine which we have already recognized to be able to display an haloperoxidase or peroxidase type activity in peroxidative halogenation, hydroxylation or oxygenation reactions of alkanes and aromatics [17], and may behave as an electron-transfer mediator in the catalytic oxidation of thiols [18,19].

(C) TECHNICAL DESCRIPTION

The invention concerns the utilization of systems, formed by complexes of vanadium (in the oxidation state +4 or +5) with di- or poly-dentate ligands coordinated by nitrogen and oxygen (N,O) or by oxygen (O,O) atoms, derived from aminoalcohols, (hydroxyimino)dicarboxylic acids, hydroxypyranones, trifluoroacetic acid, triflic acid or inorganic acids, as catalysts for the direct single-pot conversion of methane into acetic acid, either in the absence or in the presence of carbon monoxide, and in the presence of a peroxodisulfate salt ($K_2S_2O_8$), in trifluoroacetic acid ($CF_3COOH$), according to the general reaction (I).

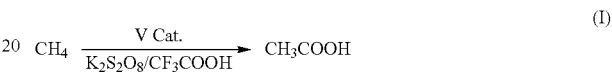

(I)

Three main types of catalysts have been considered: (i) oxovanadium(V) complexes of the type [VO(N,O-L)] [N,O-L=basic form the triethanolamine $N(CH_2CH_2O^-)_3$ or of N,N-bis(2-hydroxyethyl)glicine (bicine) $N(CH_2CH_2O^-)_2(CH_2COO^-)$], (ii) the synthetic Amavadine and its models, namely the $Ca^{2+}$ salts of the vanadium(IV) complexes, with N,O ligands, $[V(HIDPA)_2]^{2-}$ [HIDPA=basic form of 2,2'-(hydroxyimino)dipropionic acid, $^-ON\{CH(CH_3)COO^-\}_2$] and $[V(HIDA)_2]^{2-}$ [HIDA=basic form of 2,2'-hydroxyino) diacetic acid, $^-ON(CH_2COO^-)_2$], and (iii) the vanadium(V) complexes with vanadyl and O,O-ligands of the type [VO(O,O-L)$_2$] [O,O-L=basic form (maltolate) of maltol (3-hydroxy-2-methyl-4-pyrone); dibasic form (heida) of 2-hydroxyethyliminodiacetic acid, $N(CH_2CH_2OH)(CH_2COO^-)_2$; trifluoroacetate ($CF_3COO^-$); triflate ($CF_3SO_2O^-$)] and $VOSO_4$.

Illustrattive values for the turnover number (TON, moles of acetic acid per mol of metal catalyst) and for the yield (based on methane) are shown in the Table, for typical experimental conditions comprising $CH_4$:V catalyst and $K_2S_2O_8$:V catalyst molar ratios of 46:1 (corresponding to a $CH_4$ pressure of 5 atm) and 200:1, respectively, in $CF_3COOH$ at 80° C. The values indicated have been obtained commonly after 20 h reaction time, but often a much shorter period is sufficient to lead to an yield that is close to that observed after that time (e.g., entry 1 with an yield after 2 h that is already 92% of that obtained after 20 h).

The most active catalysts (the yields, based on methane, can be above 50% and the TONs approach 30) are the following ones: the triethanolamine (basic form) complex [VO{N(CH$_2$CH$_2$O)$_3$}] within those of type (i), the Amavadine models (type ii) and, among those of type (iii), [VO(O,O-L)] (O,O-L=maltolate, $CF_3COO^-$ or $CF_3SO_2O^-$). In contrast, [VO(N,O-L)] (N,O-L=bicine or heida) and the simpler $VOSO_4$ salt exhibit much lower activities.

The carboxylation of methane does not require the presence of carbon monoxide, although this gas can also act as a carbonylating agent (see below).

Methane constitutes the carbon source for the methyl group of acetic acid, as shown by the formation of $^{13}CH_3COOH$, idenfied by $^{13}C-\{^1H\}$ and $^{13}C$ NMR spectrometry, where using $^{13}C$ enriched methane. The carbonyl group of this acid should be originated, in the absence of CO, from the solvent, $CF_3COOH$, which is known [20] to react with $K_2S_2O_8$ derivatives in radical processes. The formation of acetic acid should not involve the conversion of methane into free methanol since this alcohol, under the experimental conditions used, is not converted into that acid CO can enhance the formation of acetic acid at sufficiently low pressures, suggesting that it can act as a carbonylating agent, but the effect can be minor, as observed for [VO{N(CH$_2$CH$_2$O)$_3$}]. The use of higher CO pressures (e.g. above ca. 8 atm for this catalyst and for 5 atm pressure of methane) results in an inhibiting effect.

The change of methane pressure can affect markedly the TON which, for example, increases from 5 to 28 when that pressure increases from 3 to 12 atm in the case of the [VO{N(CH$_2$CH$_2$O)$_3$}] catalyst. After reaching a maximum the yield tends to decrease when the methane pressure increases.

Higher yields can be obtained by using (i) lower methane amounts for the same pressure—e.g. the yield increases from 17% to 54% upon decreasing that amount by a factor of 2.8, in the case of Ca[V(HIDPA)$_2$]—or (ii) higher catalyst amounts—e.g. the yield increases from 24 to 43% with a fivefold increase of [VO{N(CH$_2$CH$_2$O)$_3$}] concentration, at CO and CHI pressures of 5 atm.

In any of the cases studied, the reaction does not proceed in the absence of the vanadium catalyst.

EXAMPLES

For illustrative purposes, the following description is presented for a typical experiment which can easily be adapted to other conditions:

The vanadium catalyst (0.0625 mmol) and $K_2S_2O_8$ (3.38 g, 12.5 mmol) are added to $CF_3COOH$ (23 cm$^3$) contained in a 39 cm$^3$ stainless steel autoclave which is then closed. The air is removed by dinitrogen gas flow and vacuum, whereafter methane is introduced up to the required pressure (e.g. 5 atm, 2.86 mmol) and the autoclave is heated in an oil bath at the required temperature and for the required time, with stirring of the reaction mixture. After cooling the autoclave and venting the residual gases, the autoclave is opened and the solution in the final mixture is filtered. The excess of $K_2S_2O_8$ is precipitated by addition of diethylether to the solution and is removed by filtration. The resulting solution is then analysed by gas chromatography (GC) or by gas chromatography-mass spectrometry (GC-MS).

A similar procedure is followed for the essays in the presence of CO, in which this gas is admitted to the autoclave after the introduction of methane. The essays with different reagent molar ratios, volumes of solvent or different capacities autoclaves are performed similarly.

The following complexes were prepared according to literature methods: [VO{N(CH$_2$CH$_2$O)$_3$}] [21], Ca[V(HIDPA)$_2$] [22], Ca[V(HIDA)$_2$] [22], [VO(maltolate)$_2$] [23] and [VO(CF$_3$SO$_2$O)$_2$] [24]. The new complexes [VO{N(CH$_2$CH$_2$O)$_2$(CH$_2$COO)}], [VO{N(CH$_2$CH$_2$OH)(CH$_2$COO)$_2$}(H$_2$O)] and [VO(CF$_3$COO)$_2$] were obtained by processes similar to those of [VO{N(CH$_2$CH$_2$O)$_3$}], of ref. [25] or of [VO(CF$_3$SO$_2$O)$_2$], respectively, but using the appropriate ligand. Compounds VOSO$_4$, K$_2$S$_2$O$_8$ and CF$_3$COOH were purchase from Merck and Aldrich.

REFERENCES

[1] Taniguchi, Y.; Hayashida, T.; Shibasaki H.; Piao, D.-G.; Kitamura, T.; Yamagi, T.; Fujiwara, Y. *Org Lett.* 1999, 1, 557.

[2] (a) Asadullah, M.; Taniguchi Y.; Kitamura, T.; Fujiwara, Y. *Appl. Cat. A: General* 2000, 194-195, 443.
(b) Nakata, K.; Miyata, T.; Taniguchi, Y.; Takaki K.; Fujiwara, Y. *J. Organometal. Chem.* 1995, 489, 71.
(c) Nishiguchi, T.; Nakata, K.; Takaki, K.; Fujiwara, Y. *Chem. Lett.* 1999, 1141.

[3] Asadulla, M.; Kitamura, T.; Fujiwara, Y. *Angew. Chem. Int. Ed.* 2000, 39, 2475.

[4] Nizova, G. V.; Suss-Fink G.; Stanislas, S.; Shulpin G. B. *Chem. Commun.* 1998, 1885.

[5] Lin, M; Sen, A. *Nature* 1994, 368, 613.

[6] Chepaikin, E. G.; Bezruchenko, A. P.; Leshcheva, A. A.; Boyko, G. N.; Kuzmenkov, I. V.; Grigoryan, E. H.; Shilov, A. E. *J. Mol. Catal. A—Chemical,* 2001, 169, 89.

[7] Asadullah, M.; Taniguchi Y.; Kitamura, T.; Fujiwara, Y. *Appl. Organometal. Chem.* 1998, 12, 277.

[8] Lin, M.; Sen, A. *J. Chem. Soc., Chem. Commun* 1992, 892.

[9] Bogno, A; Bukala, J.; Olah, G. A. *J. Org. Chem.* 1990, 55, 4284.

[10] Piao, D.-G.; Inoue, K.; Shibasaki, H.; Taniguchi Y.; Kitamura, T.; Fujiwara, Y. *J. Organometal. Chem.* 1999, 574, 116.

[11] Yin, G.; Piao, D.-G.; Kitamura, T.; Fujiwara, Y. *Appl. Organometal. Chem.* 2000, 14, 438.

[12] Gogate, M. R.; Spivey, J. J., WO 9959952 *[Chem. Abstr.* 1999, 131, 338610r].

[13] Sen A; Lin M., U.S. Pat. No. 5,510,525 *[Chem. Abstr.* 1996, 125, 36293m].

[14] Huang, W.; Xie, K. C.; Wang, J. P.; Gao, Z. H.; Yin, L. H.; Zhu, Q. M., *J. Catal.* 2001, 201, 100.

[15] Huang, W.; Wang, X.; Xie, K., CN 1309114, 2001.

[16] McFarlen, A. J., U.S. Pat. No. 5,659,077, WO 9735827 *[Chem. Abstr.* 1997, 127, 205287m].

[17] Reis, P. M.; Silva, J. A. L.; Fraústo da Silva, J. J. R; Pombeiro, A. J. L. *Chem. Commun.* 2000, 1845.

[18] Matoso, C. M. M.; Pombeiro, A. J. L.; Fraústo da Silva, J. A. L.; Guedes da Silva, M. F. C.; Silva, J. A. L.; Baptista-Ferreira, J. L.; Pinho-Almeida, F., in *Vanadium Compounds*, Tracey, A. S.; Crans, D. C. (Eds.), ACS Symposium Series no. 711, ACS, Washington, 1998, Ch. 18, pp. 241-247.

[19] Guedes da Silva, M. F. C.; Silva, J. A. L.; Fraústo da Silva, J. J. R; Pombeiro, A. J. L.; Amatore, C.; Verpeaux, J.-N. *J. Am. Chem. Soc.* 1996, 118, 7568.

[20] Fujiwara, Y.; Takaki, K.; Taniguchi, Y. *Synlett* 1996, 591.

[21] Crans, D. C.; Chen, H.; Anderson, O. P.; Miller, M. M. *J. Am Chem. Soc.* 1993, 115, 6769.

[22] Berry, R. E.; Armstrong, E. M; Beddoes, R. L.; Collison, D.; Ertok, S. N.; Heliwell, M.; Garner, C. D. *Angew. Chem. Int. Ed.* 1999, 38, 795.

[23] Caravan, P.; Gelmini, L.; Glover, N.; Herring, F. G.; Li, H.; McNeill, J. H.; Rettig, S. J.; Setyawati, I. A; Shuter, E.; Sun, Y.; Tracey, A. S.; Yuen, V. G.; Orvig, C. *J. Am. Chem. Soc.* 1995, 117, 12759.

[24] Chen, C. T.; Kuo, J. H.; Li, C. H.; Barhate, N. B.; Hon, S. W.; Li, T. W.; Chao, S. D.; Liu, C. C.; Li, Y. C.; Chang, I. H.; Lin, J. S.; Liu, C. J.; Chou, Y. C. *Org. Lett.* 2001, 3, 3729.

[25] Hamstra, B. J.; Houseman, A. L. P.; Colpas, G. J.; Kampt J. W.; LoBrutto, R.; Frascb, W. D.; Pecoraro, V. L. *Inorg. Chem.* 1997, 36, 4866.

TABLE

Conversion of methane into acetic acid (typical examples)[a]

| Catalyst | p(CH$_4$)[b] (atm) | p(CO)[b] (atm) | Time (h) | TON[c] | Yield[d] (%) |
|---|---|---|---|---|---|
| Type (i) | | | | | |
| [VO{N(CH$_2$CH$_2$O)$_3$}][e] | 5 | — | 2 | 9 | 20 |
| | 5 | — | 20 | 10 | 21 |
| | 5 | 5 | 20 | 11 | 24 |
| | 5 | 15 | 20 | 10 | 22 |
| | 5 | 20 | 20 | 6 | 13 |
| | 3 | 15 | 20 | 5 | 19 |
| | 8 | 15 | 20 | 25 | 34 |
| | 12 | 15 | 20 | 28 | 26 |
| | 5 | 15 | 20 | 10[f] | 35[f] |
| | 5 | 5 | 20 | 4[g] | 43[g] |
| [VO{N(CH$_2$CH$_2$O)$_2$(CH$_2$COO)}][h] | 5 | — | 20 | 2 | 5 |
| Type (ii) | | | | | |
| Ca[V(HIDPA)$_2$] | 5 | — | 2 | 7 | 15 |
| | 5 | — | 20 | 13 | 29 |
| | 5 | 5 | 20 | 10 | 21 |
| | 5 | 15 | 20 | 8 | 17 |
| | 8 | 15 | 20 | 10 | 16 |
| | 5 | 15 | 20 | 12[i] | 54[i] |
| Ca[V(HIDA)$_2$] | 5 | — | 20 | 10 | 21 |
| | 5 | 15 | 20 | 10 | 21 |
| | 12 | 15 | 20 | 28 | 25 |
| Type (iii) | | | | | |
| [VO(maltolate)$_2$][j] | 5 | — | 20 | 7 | 15 |
| | 5 | 15 | 20 | 8 | 18 |
| [VO{N(CH$_2$CH$_2$OH)(CH$_2$COO)$_2$}(H$_2$O)][k] | 5 | — | 20 | 2 | 5 |
| [VO(CF$_3$COO)$_2$][l] | 5 | — | 20 | 2 | 4 |
| | 5 | 5 | 20 | 11 | 23 |
| | 5 | 20 | 20 | 9 | 19 |
| [VO(CF$_3$SO$_2$O)$_2$][l] | 5 | — | 20 | 7 | 15 |
| | 5 | 5 | 20 | 10 | 22 |
| | 5 | 20 | 20 | 12 | 29 |
| VOSO$_4$[m] | 5 | — | 20 | 1 | 2 |
| | 5 | 20 | 20 | 2 | 5 |

[a] At the typical conditions mentioned in the experimental part and at 80° C., unless stated otherwise.
[b] Pressure measured at 25° C.
[c] Turnover number: moles of acetic acid per mol of metal catalyst.
[d] Molar yield (%) relatively to methane, i.e. moles of acetic acid per 100 moles of methane.
[e] N,O-ligand = basic form of triethanolamine.
[f] Relatively to a, a smaller amount of CH$_4$ was used (1.84 mmol), by using a greater volume of CF$_3$COOH (28 cm$^3$).
[g] Relatively to a, a fivefold amount of metal catalyst was used (0.312 mmol).
[h] N,O-ligand = basic form of N,N-bis(2-hydroxyethyl)glicine (bicine).
[i] Relatively to a, a smaller amount of methane (1.02 mmol) was used in a lower capacity reactor (23.5 cm$^3$): metal catalyst (0.046 mmol), K$_2$S$_2$O$_8$ (9.2 mmol, i.e. 200:1 catalyst), CF$_3$COOH (17 cm$^3$).
[j] Maltolate = basic form of maltol (3-hydroxy-2-methyl-4-pyrone).
[k] N,O-ligand (heida) = dibasic form of 2-hydroxyethyliminodiacetic acid (complex molecule with one H$_2$O of crystallisation).
[l] With 2H$_2$O of crystallisation per complex molecule.
[m] With 5H$_2$O per complex molecule.

The invention claimed is:

1. A process for the direct one-pot conversion of methane into acetic acid, comprising combining methane with a catalytic system comprising a vanadium complex, a peroxodisulfate salt and trifluoroacetic acid, and reacting methane with the catalytic system in the pot under mild reaction conditions, in the substantial absence of carbon monoxide.

2. The process of claim 1, wherein the vanadium complex comprises vanadium in the +4 or +5 oxidation state with one or more ligands selected from the group consisting of di- and poly-dentate ligands, coordinated by nitrogen and oxygen atoms, or by oxygen atoms, wherein said ligands are derived from aminoalcohols, (hydroxyimino)dicarboxylic acids, hydroxypyrones, trifluoroacetic acid, triflic acid or acetylacetone.

3. The process of claim 2, wherein said ligands are derived from acetylacetonate.

4. A process for the direct one-pot conversion of methane into acetic acid, comprising combining methane with a catalytic system comprising a vanadium complex, a peroxodisulfate salt and trifluoroacetic acid, and reacting methane with the catalytic system in the pot under mild reaction conditions, in the presence of carbon monoxide, wherein the vanadium complex comprises vanadium in the +4 or +5 oxidation state with one or more ligands selected from the group consisting of di- and poly-dentate ligands, coordinated by nitrogen and oxygen atoms, or by oxygen atoms, wherein said ligands are derived from aminoalcohols, (hydroxyimino)dicarboxylic acids, hydroxypyrones, trifluoroacetic acid or triflic acid.

* * * * *